(12) United States Patent
Hall et al.

(10) Patent No.: US 9,927,302 B1
(45) Date of Patent: Mar. 27, 2018

(54) IN-TOILET APPARATUS FOR DISCRIMINATION OF URINE AND FECES

(71) Applicants: David R. Hall, Provo, UT (US); Dan Allen, Springville, UT (US); Cameron Price, Provo, UT (US)

(72) Inventors: David R. Hall, Provo, UT (US); Dan Allen, Springville, UT (US); Cameron Price, Provo, UT (US)

( * ) Notice: Subject to any disclaimer, the term of this patent is extended or adjusted under 35 U.S.C. 154(b) by 0 days.

(21) Appl. No.: 15/277,499

(22) Filed: Sep. 27, 2016

(51) Int. Cl.
*G01N 33/493* (2006.01)
*G01J 5/04* (2006.01)
*A47K 13/24* (2006.01)
*E03D 11/13* (2006.01)
*G01F 23/292* (2006.01)
*G01N 33/00* (2006.01)
*G01J 5/10* (2006.01)
*G01G 19/44* (2006.01)
*G01N 5/00* (2006.01)
*G01J 5/00* (2006.01)

(52) U.S. Cl.
CPC ............. *G01J 5/041* (2013.01); *A47K 13/24* (2013.01); *E03D 11/13* (2013.01); *G01F 23/292* (2013.01); *G01G 19/44* (2013.01); *G01J 5/10* (2013.01); *G01N 5/00* (2013.01); *G01N 33/0027* (2013.01); *E03D 2201/00* (2013.01); *G01J 2005/0077* (2013.01)

(58) Field of Classification Search
CPC ........... G01N 33/493; G01N 33/54373; G01N 33/4833; E03D 11/02; E03D 1/14; E03D 5/105; G01J 5/021; G01F 23/292
See application file for complete search history.

(56) References Cited

U.S. PATENT DOCUMENTS

| | | | | |
|---|---|---|---|---|
| 2005/0261605 | A1* | 11/2005 | Shemer | A61B 10/007 600/573 |
| 2008/0035478 | A1* | 2/2008 | Wegner | C12Q 1/001 204/403.01 |
| 2012/0180731 | A1* | 7/2012 | Garner | A01K 29/005 119/417 |
| 2014/0147924 | A1* | 5/2014 | Wheeldon | G01N 21/75 436/63 |
| 2016/0083949 | A1* | 3/2016 | Plas | E03D 5/105 4/420 |

* cited by examiner

*Primary Examiner* — David Porta
*Assistant Examiner* — Faye Boosalis

(57) ABSTRACT

An in-toilet apparatus for discrimination of urine and feces is disclosed. An optical sensor is provided for the analysis of urination and defecation events within a toilet bowl. Additionally, strain gauges are provided to make possible the quantification of urine and feces that a user releases. The combination of data from the optical sensors and strain gauges makes it possible for a user to readily know the mass of their bodily excrements, characterized by excrement type. In several embodiments the optical sensor is a thermal camera mounted on the toilet seat or in the toilet bowl. In other embodiments the optical sensor is a water level sensor. In varying embodiments, strain gauges are located in the toilet seat or in an attached footscale or both.

20 Claims, 10 Drawing Sheets

IN-TOILET APPARATUS FOR DISCRIMINATION OF URINE AND FECES

BACKGROUND

Field of the Invention

The present invention relates to the measurement and characterization of human excrement.

Background of the Invention

For management of various health conditions, it is useful to track the amount of urine and feces a user passes. It is possible to track the sum of urine and feces using change in weight. However, weight alone does not discriminate the relative amounts of urine and feces. Methods such as flammable gas sensing can detect the presence of flatus or feces but not the quantity. Flammable gas sensing is also somewhat slower. Liquid level meters or divided bowls which separately collect urine and feces and which are supported by independent strain gauges could work, but these require a total redesign of the toilet system and are not compatible with a retrofitted toilet.

The addition of feces to the bowl typically causes a rapid rise in the bowl liquid level or decrease in user weight. On the other hand, the addition of urine adds volume at a slower rate and decreases user weight at a slower rate. However, some feces are small and not as easily distinguished. What is needed is a way to identify which rapid rises in bowl level or drops in user mass are due to defecation. Furthermore, a way is needed to easily identify a defecation event so as to be able to correctly ascribe a change in weight or bowl level to a defecation event rather than urination.

SUMMARY

By combining an excrement volume or mass measurement with a thermal imaging device mounted under or in a toilet seat it is possible to detect defection events. The operational assumption for this method is that the toilet bowl and feces are at different temperatures, have differing emissivity, or both such that falling excrement can be detected by an optical sensor such as a thermal imaging device, infrared wavelength camera, or optical sensor.

An in-toilet human excrement discriminating apparatus includes one or more optical sensors and one or more strain sensors. The optical sensors and the strain gauge sensors may be used to discriminate a weight of urine from a weight of feces in a user toilet session. One or more of the optical sensors may be mounted on a toilet seat. One or more of the optical sensors may be mounted in a toilet bowl. The optical sensors may have a field of view which is below a plane of the toilet seat. The optical sensors may have a field of view below a rim of the toilet bowl. The optical sensors may be a thermal imaging sensors. The optical sensors may use a medium wavelength infrared camera. The optical sensors may use a long wavelength infrared camera. The optical sensors may use a visible light camera. The toilet apparatus may include at least one bio-impedance sensor. One or more strain gauges may be located in the toilet seat and a footscale. The optical sensors may work as a combined water-level sensor and thermal imaging sensor. The combined sensor may detect water-level and thermal images with one or more optical sensors. The water-level sensor may be mounted in a toilet trapway. The optical sensor may be a photodetector. The optical sensor may be a pyrometer. The optical sensor may be a proximity detector. The toilet may include a gas sensor. The toilet may include one or more wireless transmitters or receivers. The optical sensor may be a plurality of optical sensors oriented such that a juxtaposition of input from the plurality of optical sensors provides a complete view of events within the toilet bowl.

In an example the invention is a toilet seat supported by strain gauges. A processor records the weight of a user over time while the user is seated. A drop in user mass is indicative of potential urination or defecation. If the user leans forward, which is common for users to do while defecating, the user's weight distribution shifts forward. It is useful therefore to include a footscale in front of the toilet and to record the user's weight as the sum of the weights measured by the foot scale and the seat scale. The footscale may transmit measurements wirelessly to other components of the invention. The footscale may also have bioimpedance electrodes for measuring bioimpedance to determine body composition. The invention includes a thermal camera which is mounted under the seat and arranged such that the field of view is limited to the toilet bowl, as some users may be reluctant to have a camera viewing them, even if it is just a thermal camera. The thermal camera may be arranged to look across the toilet bowl from any side. Looking from the left underside of the seat toward the right side of the bowl, urine streams are visible in the camera field of view as a warm streak directed down and slightly forward or left in the camera field of view. Urination events have a distinctive thermal image or thermal pattern allowing the urination events to be distinguished from fecal events. Feces introduce a warm streak in the camera field of view which is directed primarily downwards and is further to the right in the field of view. Defecation events have a distinctive thermal image or thermal pattern allowing the defecation events to be distinguished from urination events. Defecation events and urination events may be compared to thermal patterns generated by the toilet bowl, body parts of the toilet user, water in the toilet bowl, and/or by comparison of thermal patterns of previous events. Thermal patterns of previous and instant defecation events and of urination events may be compared to each other in order to distinguish a urination event from a defecation event. A urination event has a different thermal signature compared to a thermal signature of a defecation event because of differences in mass, thermal conductivity, heat conduction, and temperature. Detection of body-temperature range objects in the right side of the field of view allows the controller to assign large changes in mass to defecation events. Other changes in mass would be due to urination.

In another example a capacitive liquid level meter is attached to the side of the bowl either inside the bowl or outside the bowl. A controller reads out the liquid level and when a defecation event is detected by the thermal camera the change in liquid level can be ascribed to feces. The bowl level has to be calibrated. This can be done by repeatedly pouring a known amount of liquid into the bowl. For this to work the bowl level has to be lower than the trap level. This is not typical in toilets which rely on a 2" column of water in the trapway to provide isolation from sewer gases. However, a toilet can be designed with more than a 2" height in the trapway and the tank or bowl refill device set to return the liquid level to slightly below the trap height after a flush. The capacitive sensor could also be in the trapway or in a flush jet fill tube/port which directs water from the tank or water pipes to a port below the water level, providing a so-called "jet" which has the function of rapidly filling the trapway during a flush to create a siphon with a minimum of water.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
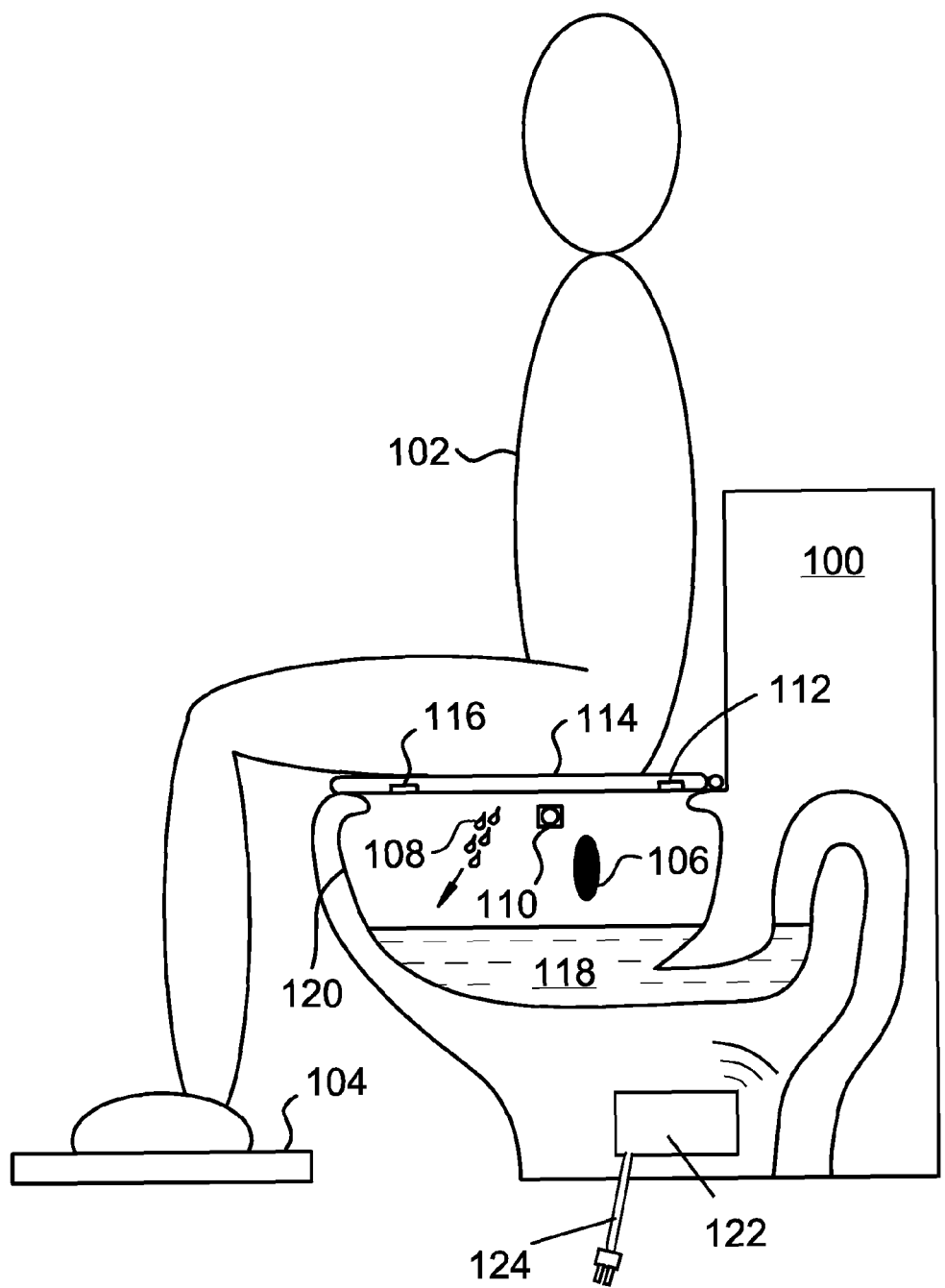
FIG. 1 shows a side cross-sectional view of the in-toilet human excrement discriminating apparatus in use.

Referring to FIG. 1, a toilet 100 comprises an in-toilet human excrement discriminating system that comprises an optical sensor 110, strain gauges 112 and 116, and a footscale 104. A toilet seat 114 may comprise strain gauges 112 and 116, and/or additional strain gages may be located on or near hinges of toilet seat 114 and in footstool 104. In this embodiment the optical sensor 110 may be a thermal imaging sensor, a medium wavelength infrared camera, a long wavelength infrared camera, or a visible light camera. The optical sensor may work as a combined water-level sensor and thermal imaging sensor. The combined sensor may detect water-level and thermal images with one or more optical sensors. A user 102 is shown seated on the toilet seat 114 releasing feces 106 and urine 108. The optical sensor 110 is mounted in such a way as to view an interior space of a toilet bowl 120 and more specifically the feces 106 and urine 108. Defecation events have a distinctive thermal image or thermal pattern allowing the defecation events to be distinguished from urination events. Defecation events and urination events may be compared to thermal patterns generated by one or more of the following: the toilet bowl, body parts of the toilet user, water in the toilet bowl, and/or by comparison of thermal patterns of previous elimination events. Thermal patterns of previous and instant defecation events and of urination events may be compared to each other in order to distinguish a urination event from a defecation event. A urination event has a different thermal signature compared to a thermal signature of a defecation event because of differences in mass, thermal conductivity, heat conduction, and temperature. The field of view of the optical sensor 110 may originate on a side, front or back of toilet bowl 120 and expands outward to include water 118, urine 108, and feces 106. The optical sensor 110 may be oriented such that buttocks of the user 102 are not within the field of view of the optical sensor 110. Additional optical sensors 110 may form an array of optical sensors used to expand a field of view of an inner area of toilet 100. Additional sensors may be located in a contiguous linear sensor array or be positioned at different locations around toilet bowl 120.

Toilet 100 may contain a controller 122, and power source 124. Power source 124 may be battery power, generator power, or a wired power connection. Controller 122 may contain one or more processors, memory, and wireless/wired transceivers for communicating data to remote computers, user devices, and remote databases. Controller 122 may be operably connected to one or more toilet sensors such as image sensors, thermal image sensors, capacitive sensors, inductive sensors, level sensors, weight sensors, and force sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 2:
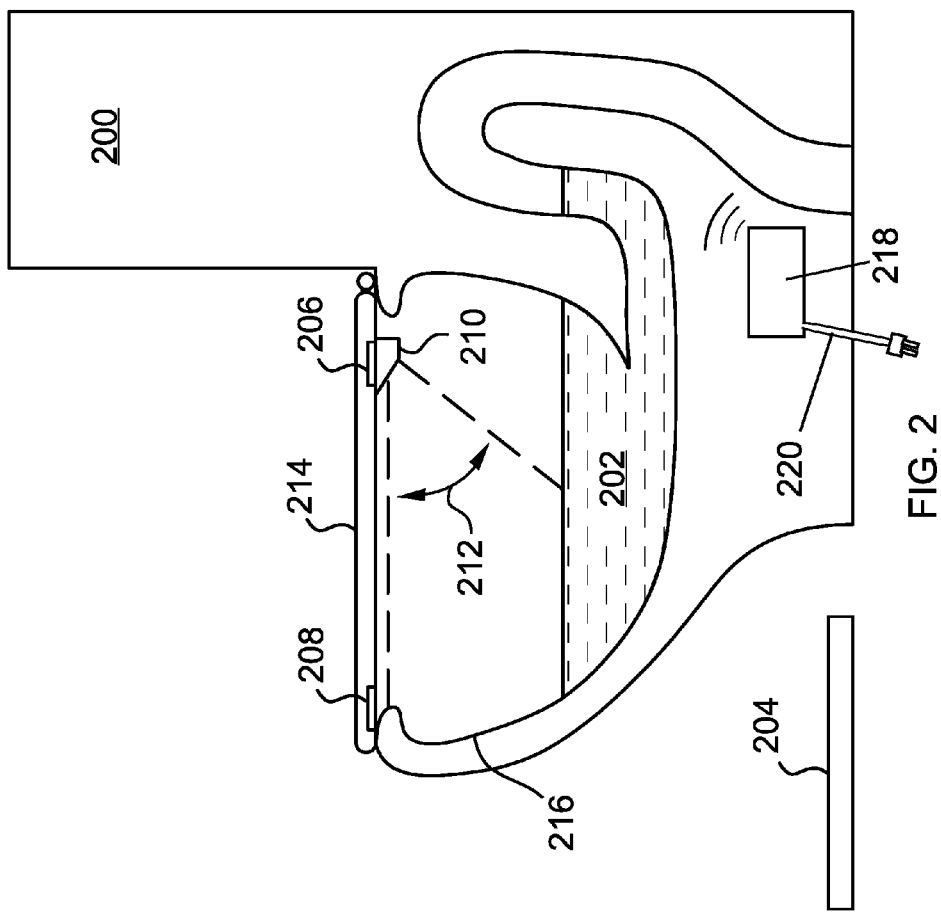
FIG. 2 shows a side cross-sectional view of the in-toilet human excrement discriminating apparatus in accordance with an embodiment of the invention.

FIG. 2 shows a toilet 200 comprising an in-toilet human excrement discriminating apparatus comprising an optical sensor 210, strain gauges 208 and 206, and a footscale 204. A toilet seat 214 comprises the strain gauges 208 and 206 and the optical sensor 210. The optical sensor 210 may be a thermal imaging sensor, a medium wavelength infrared camera, a long wavelength infrared camera, or a visible light camera. The optical sensor may work as a combined water-level sensor and thermal imaging sensor. The combined sensor may detect water-level and thermal images with one or more optical sensors. The optical sensor 210 comprises a field of view 212 wherein no portion of the field of view 212 extends beyond confines of a toilet bowl 216 comprised in the toilet 200 and includes some or all of water 202 in the toilet bowl 216.

Toilet 200 may contain a controller 218, and power source 220. Power source 220 may be battery power, generator power, or a wired power connection. Controller 218 may contain one or more processors, memory, and wireless/wired transceivers for communicating data to remote computers, user devices, and remote databases. Controller 218 may be operably connected to one or more toilet sensors such as image sensors, thermal image sensors, capacitive sensors, inductive sensors, level sensors, weight sensors, and force sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 3:
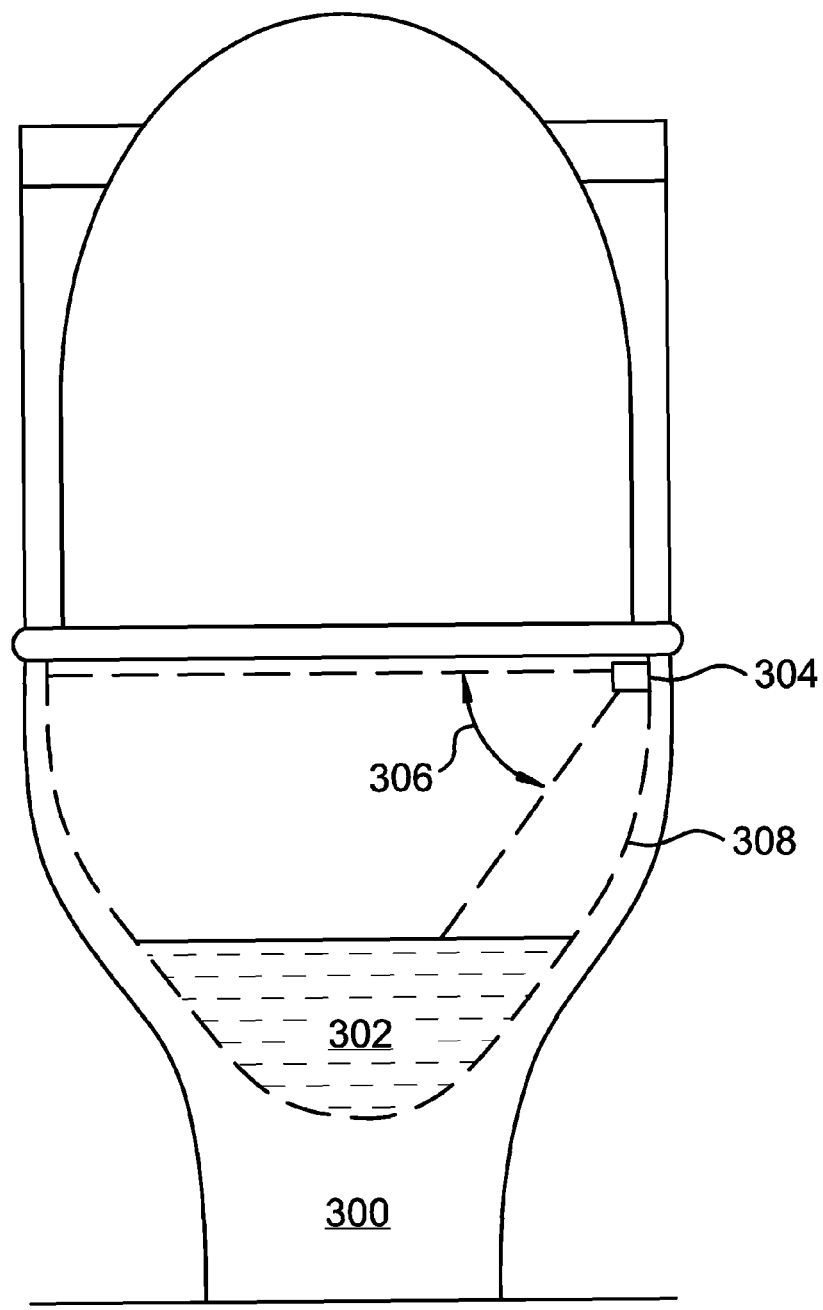
FIG. 3 is frontal cross-sectional view of the in-toilet human excrement discriminating apparatus.

FIG. 3 shows a toilet 300 comprising an in-toilet human excrement discriminating apparatus that comprises an optical sensor 304 mounted in a toilet bowl 308. The optical sensor 304 may be a thermal imaging sensor, a medium wavelength infrared camera, a long wavelength infrared camera, or a visible light camera. The optical sensor may work as a combined water-level sensor and thermal imaging sensor. The combined sensor may detect water-level and thermal images with one or more optical sensors. The optical sensor 304 comprises a field of view 306, which is oriented on an interior side of toilet bowl 308, with an upper limit of the field of view 306 not extending outside the confines of the toilet bowl 308, and with a lower limit that includes some or all of the water 302.

Figure 4:
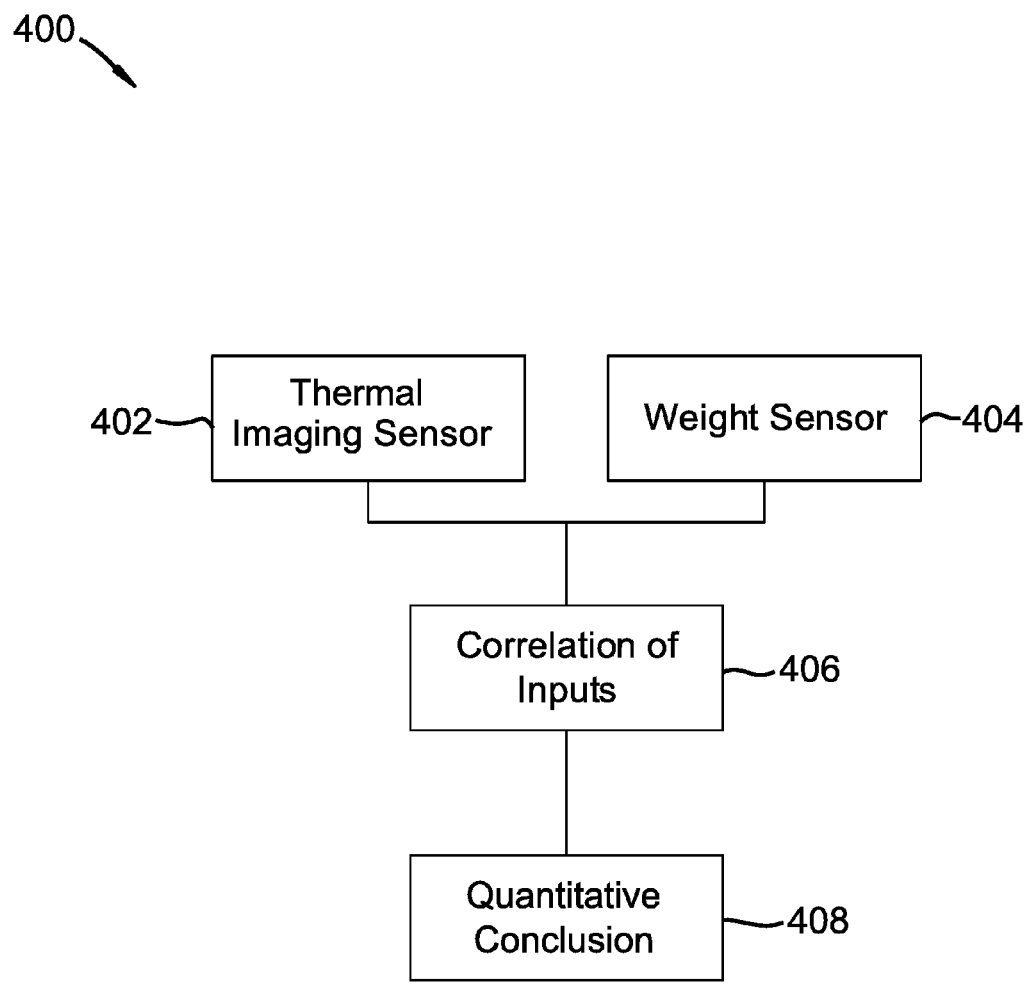
FIG. 4 charts the flow of functions in an embodiment of the in-toilet human excrement discriminating apparatus using a thermal imaging device.

FIG. 4 shows a stepwise method 400 for operation of an in-toilet human excrement discriminating apparatus wherein a thermal imagining sensor 402 and a strain gauge or gauges 404 supply data that undergoes correlation 406. The correlation 406 may be performed locally through a processor in the toilet or remotely in a database server and is subsequently used to make a conclusion 408 of specific quantities of various excrements. Such correlation and determination may be used to discount fluctuations in mass not caused by defecation or urination. Thermal imaging sensor 402, a processor, and memory may detect a urination event or defecation event, a weight event, and store the events associated with a time of the events and correlate the events and the times to distinguish a urination weight event from a defecation weight event. Additionally, or alternatively, thermal image data may be used to correlate a volume of urine with a urination event using weight data and a volume of defecation with a defecation event using weight data to obtain a quantitative conclusion 408.

Figure 5:
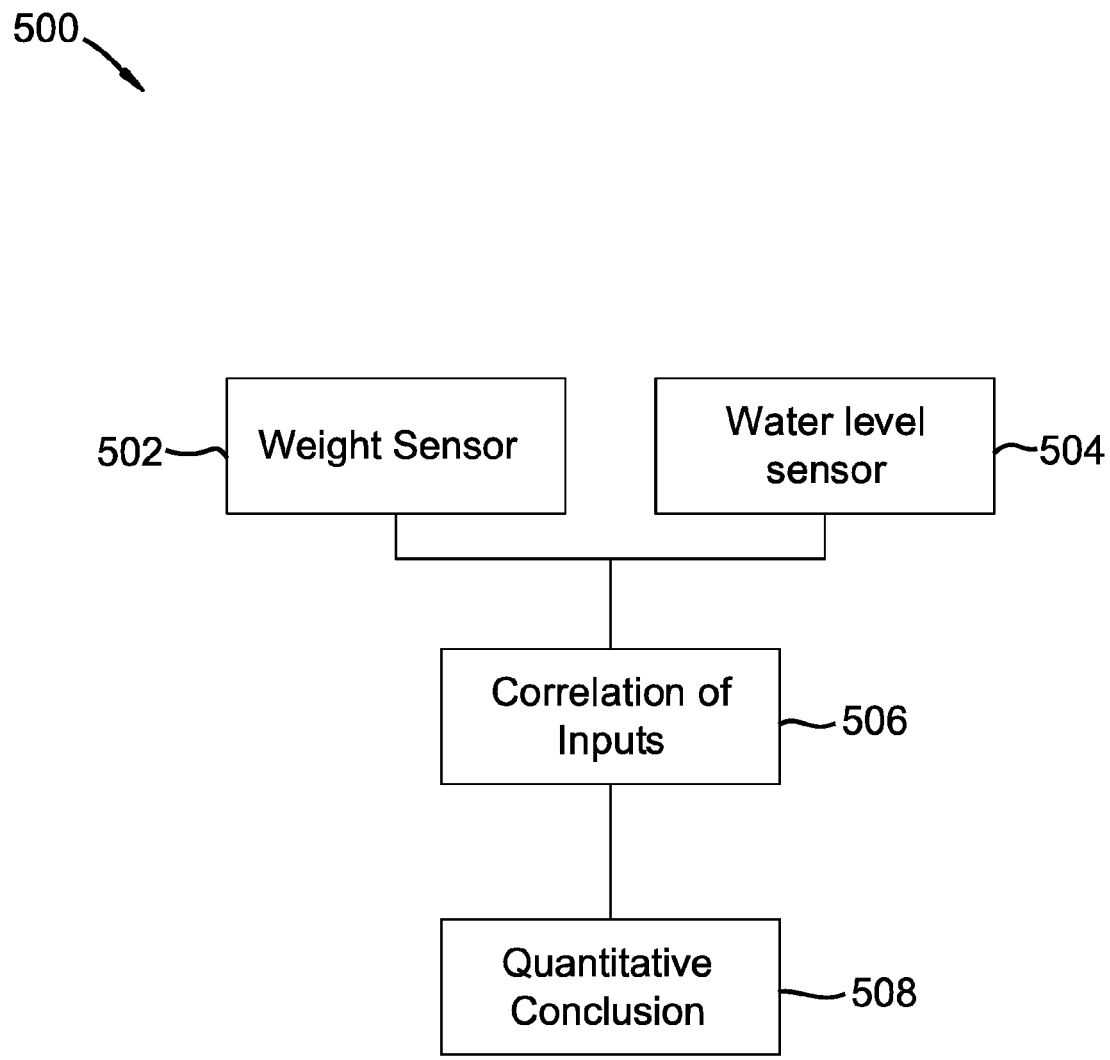
FIG. 5 charts the flow of functions in an embodiment of the in-toilet human excrement discriminating apparatus using a water level sensor.

FIG. 5 shows a stepwise method 500 for operation of an in-toilet human excrement discriminating apparatus wherein a water level sensor 504 and a strain gauge or sensors 502 supply data that undergoes correlation 506. The correlation 506 is subsequently used to make a conclusion 508 of specific quantities of various excrements.

The correlation 506 may be performed locally through a processor in the toilet or remotely in a database server and is subsequently used to make a conclusion 508 of specific quantities of various excrements. Such correlation and determination may be used to discount fluctuations in mass not caused by defecation or urination. Weight sensors 502, a processor, and memory may detect a urination event and/or defecation event, a water level change, and store the events associated with a time of the events and correlate the events and the times to distinguish a urination weight event from a defecation weight event. Additionally, or alternatively, thermal image data may be used to correlate a volume of urine with a urination event using weight data and a volume of defecation with a defecation event using weight data and water level sensor data to obtain a quantitative conclusion 508.

Figure 6:
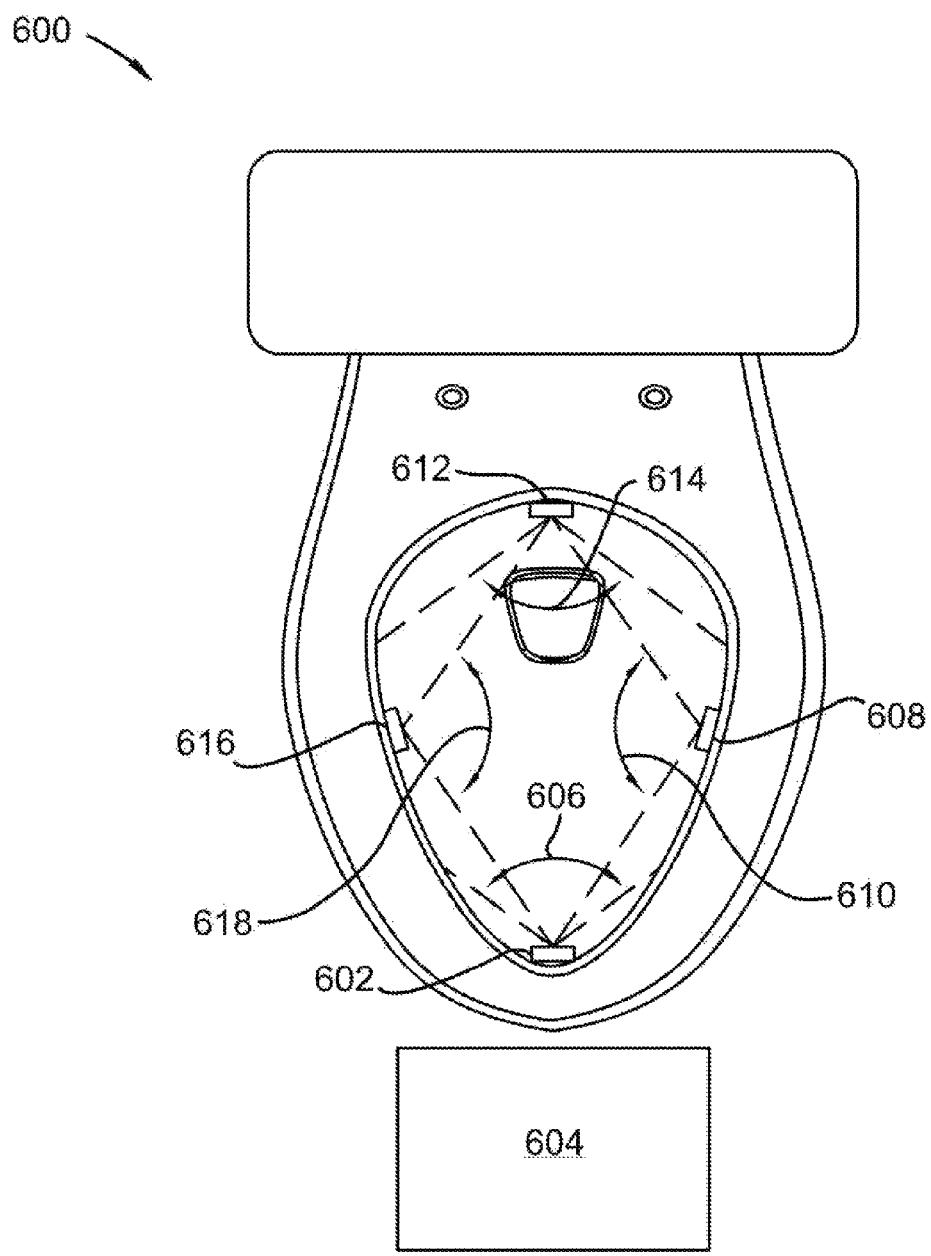
FIG. 6 is a top down view of the in-toilet human excrement discriminating apparatus.

FIG. 6 shows a top down view of toilet 600 comprising an in-toilet human excrement discriminating apparatus that comprises optical sensors 602, 608, 612, and 616 that comprise fields of view 606, 610, 614, and 618 respectively. The in-toilet human excrement discriminating apparatus further comprises a footscale 604. The optical sensors 602, 608, 612, and 616 are mounted such that an aggregate view created by the fields of view 606, 610, 614, and 618 includes all of the interior space of the bowl of toilet 600. The optical sensors may work as a combined water-level sensor and thermal imaging sensor. The combined sensor may detect water-level and thermal images with one or more optical sensors. The aggregate view will allow for more comprehensive analysis of urination and defecation events. The optical sensors 602, 608, 612, and 616 may be any combination of thermal imaging sensors, medium wavelength infrared cameras, long wavelength infrared cameras, visible light cameras, or water level sensors. A comprehensive view of the toilet bowl may allow for volumetric measurement of human excrement, which can be used to calculate fecal density (using volume and mass data) when the data is used in tandem with weight data from the footscale 604.

Figure 7:
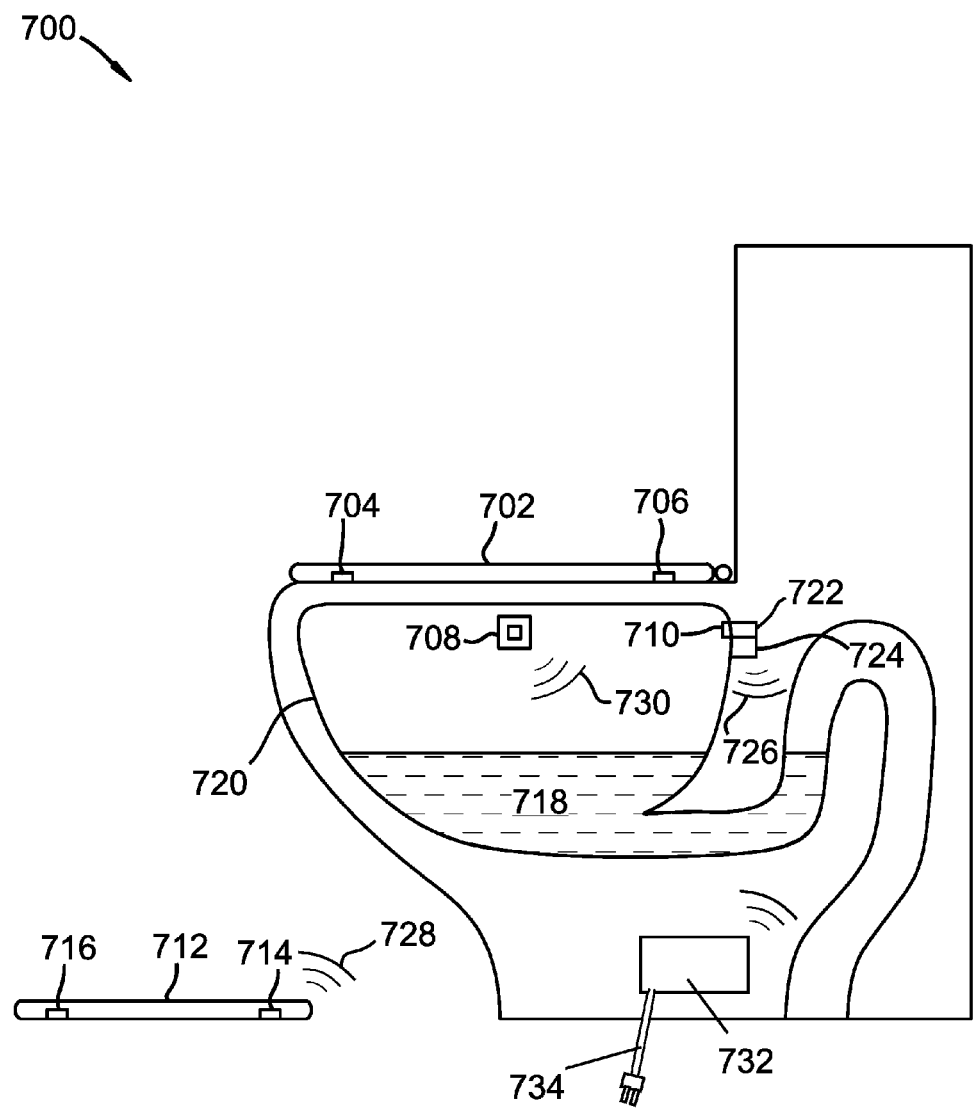
FIG. 7 is a side cross-sectional view of the in-toilet human excrement discriminating apparatus with a gas sensor.

FIG. 7 shows a toilet 700 comprising an in-toilet human excrement discriminating apparatus that comprises an optical sensor 708, strain gauges 704, 706, 714, and 716, a gas sensor 710, a processor 722, and a wireless transceiver 724. The wireless transceiver 724 allows for wireless communication 726, 730, and 728 such that the processor can wirelessly accept input from the gas sensor 710, optical sensor 708, and strain gauges 716, 714, 704, and 706 and perform necessary correlations and calculations. The optical sensor may work as a combined water-level sensor and thermal imaging sensor. The combined sensor may detect water-level and thermal images with one or more optical sensors. A toilet seat 702 comprises the strain gauges 704 and 706. A footscale 712 comprises the strain gauges 714 and 716. The toilet 700 additionally comprises a toilet bowl 720 and water 718, wherein the gas sensor 710 is used to detect chemical constituents of gases in the toilet bowl. Data from the gas sensor 710 may assist in identifying a presence of urine, feces, or other bodily excrement and relative quantities of such excrements.

Toilet 700 may contain a controller 732, and power source 734. Power source 734 may be battery power, generator power, or a wired power connection. Controller 732 may contain one or more processors, memory, and wireless/wired transceivers for communicating data to remote computers, user devices, and remote databases. Controller 732 may be operably connected to one or more toilet sensors such as image sensors, thermal image sensors, capacitive sensors, inductive sensors, level sensors, weight sensors, and force sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 8:
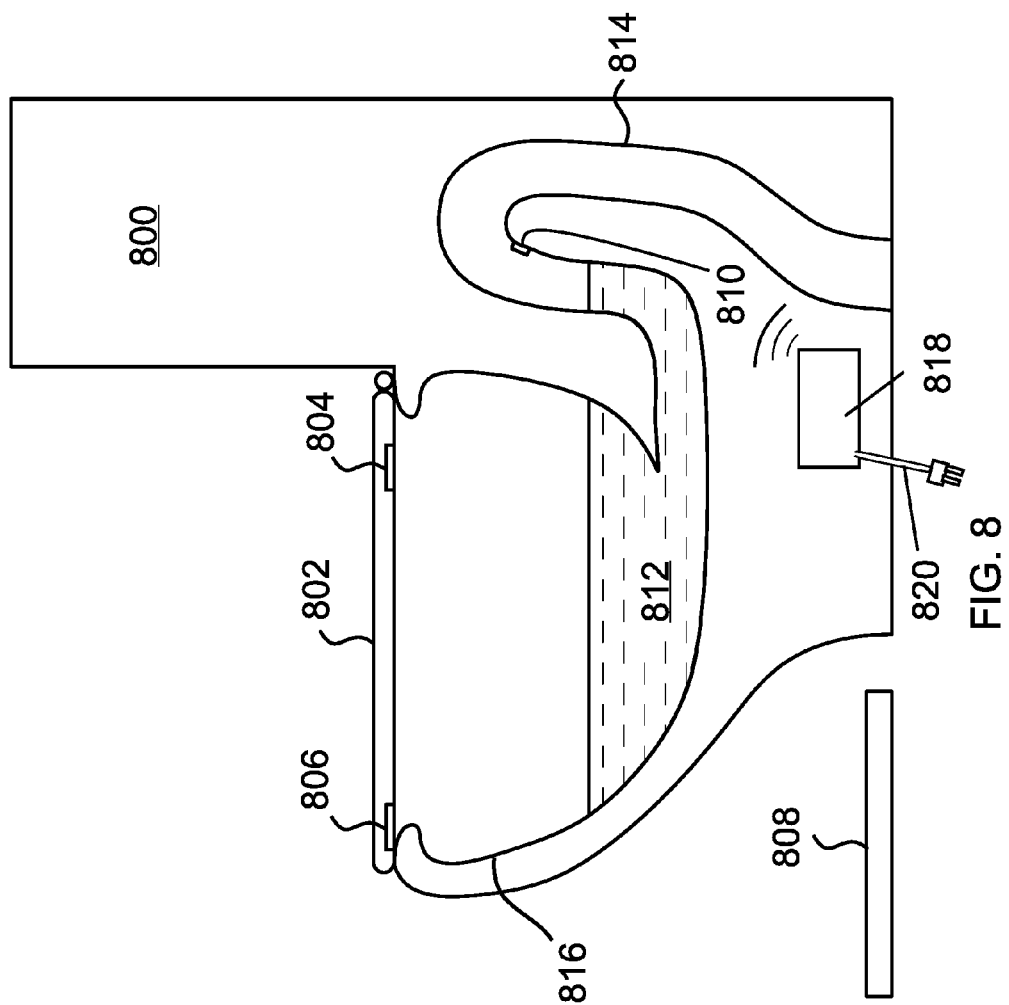
FIG. 8 is a side cross-sectional view of the in-toilet human excrement discriminating apparatus with an optical sensor in the toilet trapway.

FIG. 8 shows a toilet 800 comprising an in-toilet human excrement discriminating apparatus that comprises an optical sensor 810, strain gauge 804 and 806, and a footscale 808. The toilet 800 further comprises a channel 814, a toilet seat 802, and a toilet bowl 816. The optical sensor 810 may be a water level sensor to sense the level of water 812. The optical sensor may work as a combined water-level sensor and thermal imaging sensor. The combined sensor may detect water-level and thermal images with one or more optical sensors. Input from the optical sensor 810 may be correlated with input from the strain gauges 804 and 806 and the footscale 808 in order to discriminate between defecation and urination events based on mass fluctuations and changes in the level of the water 812.

Toilet 800 may contain a controller 818, and power source 820. Power source 820 may be battery power, generator power, or a wired power connection. Controller 818 may contain one or more processors, memory, and wireless/wired transceivers for communicating data to remote computers, user devices, and remote databases. Controller 818 may be operably connected to one or more toilet sensors such as image sensors, thermal image sensors, capacitive sensors, inductive sensors, level sensors, weight sensors, and force sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 9:
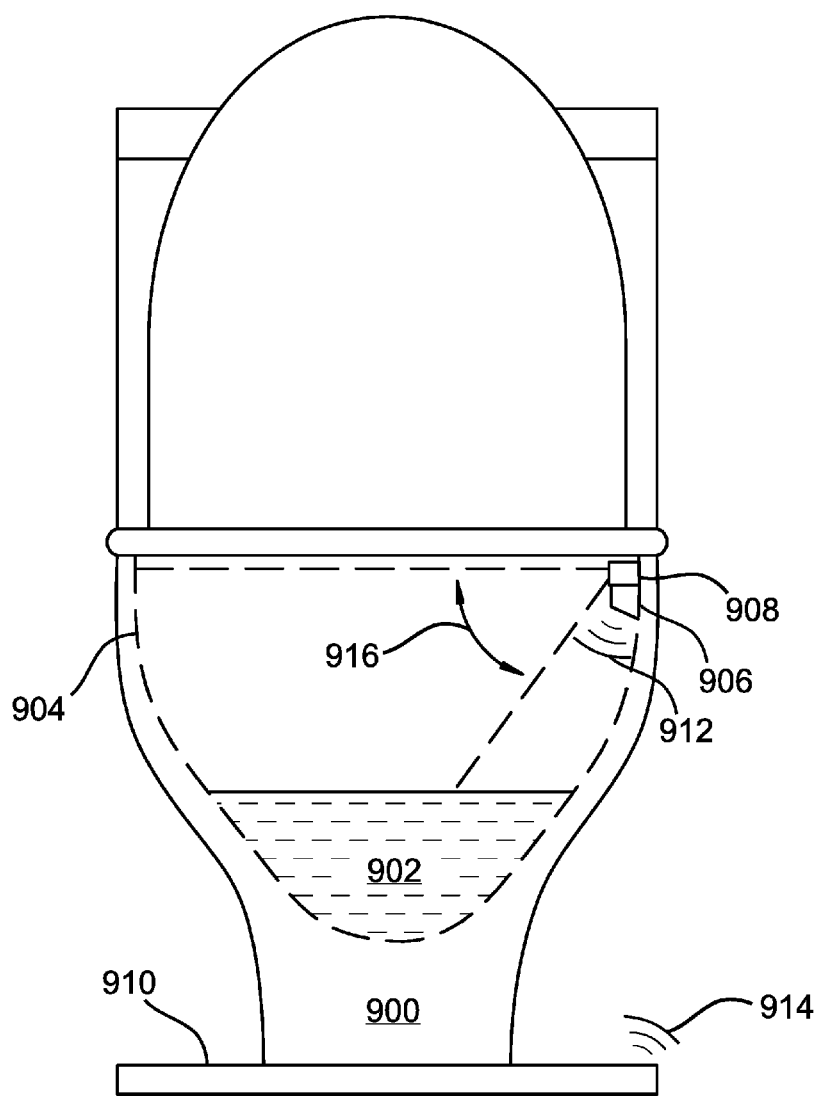
FIG. 9 is a front cross-sectional view of the in-toilet human excrement discriminating apparatus in accordance with an embodiment of the invention.

FIG. 9 shows a toilet 900 comprising a toilet bowl 904, water 902, and an in-toilet human excrement discriminating apparatus that comprises a footscale 910, a processor 906, and an optical sensor 908. The optical sensor 908 comprises a field of view 916. The footscale 910 and processor 906 comprise wireless communication capabilities 914 and 912 respectively. The processor 906 and the optical sensor 908 are mounted on a side of the toilet bowl 904. The optical sensor may work as a combined water-level sensor and thermal imaging sensor. The combined sensor may detect water-level and thermal images with one or more optical sensors. The footscale 910 may wirelessly transmit data to the processor 906 which also receives data from optical sensor 908. These two inputs may be used to quantify an amount of feces or urine a user releases.

Figure 10:
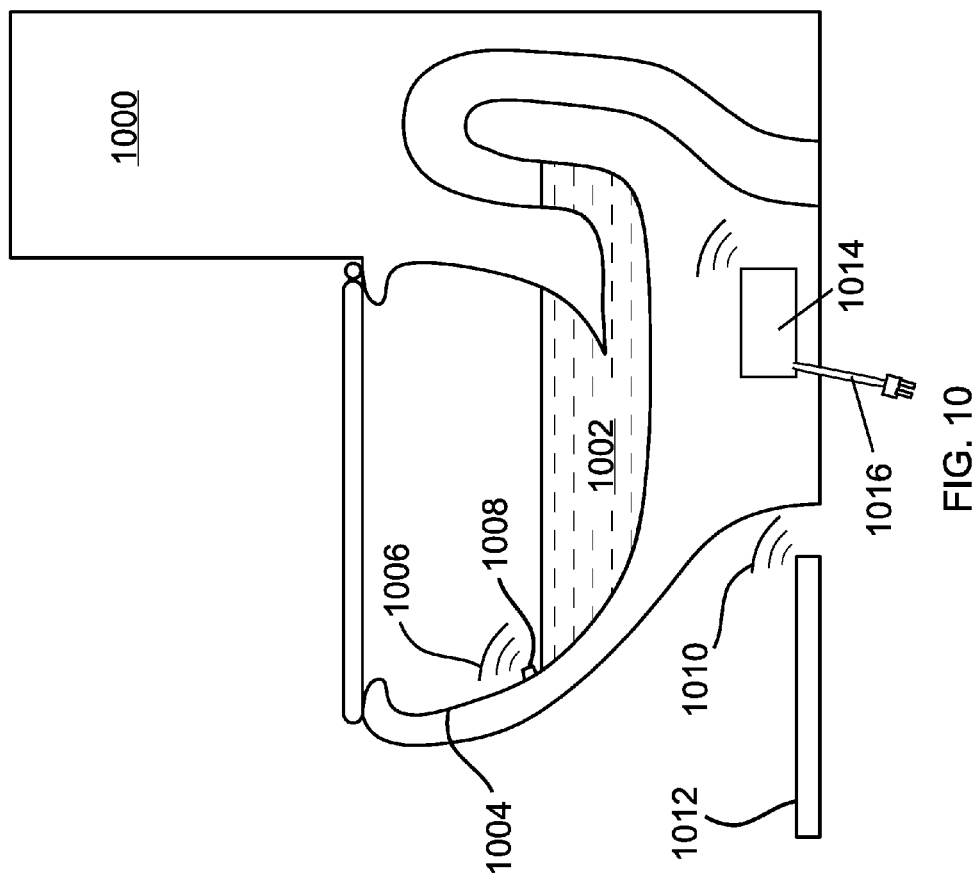
FIG. 10 is a side cross-sectional view of the in-toilet human excrement discriminating apparatus wherein the optical sensor is a water-level sensor mounted in the toilet bowl.

FIG. 10 shows a toilet 1000 comprising a toilet bowl 1004, water 1002, and an in-toilet human excrement discriminating apparatus that comprises an optical sensor 1008, and a footscale 1012. The optical sensor 1008 and the footscale 1012 comprise wireless communication capabilities 1006 and 1010 respectively. In this embodiment the optical sensor 1008 may be a water level sensor mounted on an interior surface of the toilet bowl 1004 used to indicate changes in the level of the water 1002. The optical sensor 1008 may work as a combined water-level sensor and thermal imaging sensor. The combined sensor may detect water-level and thermal images with one or more optical sensors. The optical sensor 1008 may communicate wirelessly with the footscale 1012 in order attribute the changes in water level to certain mass fluctuations of a user. These attributions may be used to quantify the amount of urine or feces a user releases.

Toilet 1000 may contain a controller 1014, and power source 1016. Power source 1016 may be battery power, generator power, or a wired power connection. Controller 1014 may contain one or more processors, memory, and wireless/wired transceivers for communicating data to remote computers, user devices, and remote databases. Controller 1014 may be operably connected to one or more toilet sensors such as image sensors, thermal image sensors, capacitive sensors, inductive sensors, level sensors, weight sensors, and force sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An in-toilet human excrement discriminating apparatus comprising:
   an optical sensor;
   one or more strain gauges;
   wherein an output of the optical sensor and an output of the strain gauge are used to discriminate a weight of urine from a weight of feces in a user toilet session.

2. The in-toilet human excrement discriminating apparatus of claim 1, wherein the optical sensor is mounted on a toilet seat.

3. The in-toilet human excrement discriminating apparatus of claim 2, wherein the optical sensor has a field of view which is below a plane of the toilet seat.

4. The in-toilet human excrement discriminating apparatus of claim 1, wherein the optical sensor is mounted in a toilet bowl.

5. The in-toilet human excrement discriminating apparatus of claim 4, wherein the optical sensor has a field of view below a rim of the toilet bowl.

6. The in-toilet human excrement discriminating apparatus of claim 4, wherein the optical sensor is a plurality of optical sensors oriented such that a juxtaposition of input from the plurality of optical sensors provides a complete view of events within the toilet bowl.

7. The in-toilet human excrement discriminating apparatus of claim 1, wherein the optical sensor is a thermal imaging sensor.

8. The in-toilet human excrement discriminating apparatus of claim 1, wherein the optical sensor is a medium wavelength infrared camera.

9. The in-toilet human excrement discriminating apparatus of claim 1, wherein the optical sensor is a long wavelength infrared camera.

10. The in-toilet human excrement discriminating apparatus of claim 1, wherein the optical sensor is a visible light camera.

11. The in-toilet human excrement discriminating apparatus of claim 1, further comprising at least one bio-impedance sensor.

12. The in-toilet human excrement discriminating apparatus of claim 1, wherein the one or more strain gauges are located in the toilet seat and a footscale.

13. The in-toilet human excrement discriminating apparatus of claim 12, further comprising one or more wireless transmitters or receivers.

14. The in-toilet human excrement discriminating apparatus of claim 1, wherein the optical sensor is a water-level sensor.

15. The in-toilet human excrement discriminating apparatus of claim 14, wherein the water-level sensor is mounted in a toilet trapway.

16. The in-toilet human excrement discriminating apparatus of claim 1, further comprising a processor.

17. The in-toilet human excrement discriminating apparatus of claim 1, wherein the optical sensor is a photodetector.

18. The in-toilet human excrement discriminating apparatus of claim 1, wherein the optical sensor is a pyrometer.

19. The in-toilet human excrement discriminating apparatus of claim 1, wherein the optical sensor is a proximity detector.

20. The in-toilet human excrement discriminating apparatus of claim 1, further comprising a gas sensor.

* * * * *